US00PP20096P2

(12) United States Plant Patent
Oudshoorn

(10) Patent No.: US PP20,096 P2
(45) Date of Patent: Jun. 16, 2009

(54) ***GERANIUM* PLANT NAMED 'THUMBLING HEARTS'**

(50) Latin Name: *Geranium cinereum*
Varietal Denomination: Thumbling Hearts

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/999,290

(22) Filed: Dec. 4, 2007

(51) Int. Cl.
*A01H 5/00* (2006.01)

(52) U.S. Cl. ..... Plt./324
(58) Field of Classification Search ..... Plt./324
See application file for complete search history.

*Primary Examiner*—Kent L Bell
(74) *Attorney, Agent, or Firm*—C. A. Whealy

(57) ABSTRACT

A new and distinct cultivar of *Geranium* plant named 'Thumbling Hearts', characterized by its upright and outwardly spreading plant habit; strong growth habit; freely basal branching habit; dark green-colored leaves; freely flowering habit; light pink-colored flowers with red purple-colored venation and centers; and good garden performance.

2 Drawing Sheets

Botanical designation: *Geranium cinereum.*
Cultivar denomination: 'Thumbling Hearts'.

BACKGROUND OF THE INVENTION

The present invention relates to a new and distinct cultivar of *Geranium,* botanically known as *Geranium cinereum,* and hereinafter referred to by the name 'Thumbling Hearts'.

The new *Geranium* is a product of a planned breeding program conducted by the Inventor in Rijpwetering, The Netherlands. The objective of the breeding program is to create new strong and healthy *Geranium* cultivars with attractive flowers.

The new *Geranium* originated from a cross-pollination made by the Inventor in July, 2002, of the *Geranium cinereum* cultivar Purple Pillow, not patented, as the female, or seed, parent with the *Geranium cinereum* cultivar Ballerina, not patented as the male, or pollen, parent. The new *Geranium* was discovered and selected by the Inventor as a single flowering plant from within the progeny of the stated cross-pollination grown in a controlled environment in Rijpwetering, The Netherlands in February, 2003.

Asexual reproduction of the new *Geranium* by divisions in a controlled environment in Rijpwetering, The Netherlands, has shown that the unique features of this new *Geranium* are stable and reproduced true to type in successive generations.

SUMMARY OF THE INVENTION

The cultivar Thumbling Hearts has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Thumbling Hearts'. These characteristics in combination distinguish 'Thumbling Hearts' as a new and distinct cultivar of *Geranium:*

1. Upright and outwardly spreading plant habit.
2. Strong growth habit.
3. Freely basal branching habit.
4. Dark green-colored leaves.
5. Freely flowering habit.
6. Light pink-colored flowers with red purple-colored venation and centers.
7. Good garden performance.

Plants of the new *Geranium* differ primarily from plants of the female parent, the cultivar Purple Pillow, primarily in flower color as plants of the cultivar Purple Pillow have warm purple-colored flowers.

Plants of the new *Geranium* differ primarily from plants of the male parent, the cultivar Ballerina, primarily in flower color as plants of the cultivar Ballerina have darker pink-colored flowers.

Plants of the new *Geranium* can be compared to plants of the *Geranium cinereum* cultivar Carol, disclosed in U.S. Plant Pat. No. 14,124. In side-by-side comparisons conducted in Rijpwetering, The Netherlands, plants of the new *Geranium* differed primarily from plants of the cultivar Carol in flower color as plants of the cultivar Carol had purple-colored flowers.

BRIEF DESCRIPTION OF THE PHOTOGRAPHS

The accompanying colored photographs illustrate the overall appearance of the new *Geranium,* showing the colors as true as it is reasonably possible to obtain in colored reproductions of this type. Colors in the photographs may differ slightly from the color values cited in the detailed botanical description which accurately describe the colors of the new *Geranium.*

The photograph on the first sheet comprises a side perspective view of typical flowering plants of 'Thumbling Hearts' grown in an outdoor nursery.

The photograph at the top of the second sheet is a close-up view of a typical flower and leaves of 'Thumbling Hearts'.

The photograph at the bottom of the second sheet is a close-up view of typical leaves of 'Thumbling Hearts'.

DETAILED BOTANICAL DESCRIPTION

The aforementioned photographs and following observations, measurements and values describe plants grown in Rijpwetering, The Netherlands in an outdoor nursery during the summer. During the production of the plants, day temperatures ranged from 14° C. to 32° C., night temperatures ranged from 7° C. to 15° C. and light levels ranged from 10,000 lux to 50,000 lux. Plants were about one year old when the photographs and the description were taken. In the detailed description, color references are made to The Royal Horticultural Society Colour Chart, 2001 Edition, except where general terms of ordinary dictionary significance are used.

Botanical classsification: *Geranium cinereum* cultivar Thumbling Hearts.

Parentage:

*Female, or seed, parent.*—*Geranium cinereum* cultivar Purple Pillow, not patented.

*Male or pollen parent.*—*Geranium cinereum* cultivar Ballerina, not patented.

Propagation:

*Type.*—By divisions.

*Time to produce a rooted young plant, summer.*—About 20 weeks.

*Root description.*—Fine, moderately fibrous; N170A in color.

*Rooting habit.*—Moderately dense.

Plant description:

*General appearance.*—Herbaceous perennial. Upright and outwardly spreading plant habit; flattened globular in shape.

*Growth and branching habit.*—Moderately vigorous growth habit. Freely basal branching habit with about 13 lateral branches developing per plant.

*Plant height, to top of umbels.*—About 19.4 cm.

*Plant width.*—About 44.5 cm.

*Lateral branches.*—Length: About 24.1 cm. Diameter: About 1.8 mm. Internode length: About 4.1 cm. Texture: Densely pubescent. Strength: Moderately strong. Color: 144A; upper surface flushed with 177B to 177C.

Foliage description:

*Arrangement.*—Basal and alternate stem leaves; simple.

*Length, basal leaves.*—About 2.6 cm.

*Length, stem leaves.*—About 1.4 cm.

*Width, basal leaves.*—About 3 cm.

*Width, stem leaves.*—About 1.7 cm.

*Shape, basal and stem leaves.*—Orbicular.

*Apex, basal and stem leaves.*—Acute.

*Base, basal and stem leaves.*—Hastate.

*Margin, basal leaves.*—Palmately cleft; lobes crenate.

*Margin, stem leaves.*—Palmately cleft; lobes entire.

*Venation pattern, basal and stem leaves.*—Palmate.

*Texture, upper and lower surfaces, basal and stem leaves.*—Moderately pubescent.

*Color, basal and stem leaves.*—Developing foliage, upper surface: 137B. Developing foliage, lower surface: 138B. Fully developed, upper surface: 137A; venation, 144B to 144C. Fully developed, lower surface: 138A; venation, 144D.

*Petiole.*—Length, basal leaves: About 8.5 cm. Length, stem leaves: About 1.1 cm. Diameter, basal leaves: About 1 mm. Diameter, stem leaves: About 0.8 mm. Texture, upper and lower surfaces, basal and stem leaves: Pubescent. Color, upper and lower surfaces, basal and stem leaves: 144A.

Flower description:

*Flower arrangement.*—Single rotate flowers arranged in pairs arising from apical leaf axils. Flowers face upright to slightly outward. Flowers not fragrant.

*Quantity of flowers.*—Freely flowering habit; about 24 flower buds and open flowers per lateral branch.

*Flowering season.*—In The Netherlands, flowering is continuous from late spring to late summer. Flowers not persistent.

*Flower longevity.*—Flowers last about one week on the plant.

*Flower diameter.*—About 3.2 cm.

*Flower depth (height).*—About 1.1 cm.

*Flower buds.*—Length: About 8 mm. Diameter: About 4.5 mm. Shape: Elliptic to obovate. Color: 137C.

*Petals.*—Quantity per flower: Five in a single whorl. Length: About 1.7 cm. Width: About 1.4 cm. Shape: Obcordate. Apex: Emarginate. Base: Attenuate. Margin: Entire. Texture, upper and lower surfaces: Mostly smooth; towards the base, densely pubescent. Color: When opening and fully opened, upper surface: Lighter than 77D; towards the base, N74A; venation, N78A; venation towards the base, N79A. When opening and fully opened, lower surface: Lighter than 77D; towards the base, 72A to 72B; venation, N78A; venation towards the base, N79A.

*Sepals.*—Quantity per flower: Five, arranged in a single whorl. Length: About 1 cm. Width: About 4 mm. Shape: Elliptic. Apex: Mucronate. Base: Cuneate. Margin: Entire. Texture, upper and lower surfaces: Densely pubescent. Color: When opening, upper surface: 143A to 143B. When opening, lower surface: 137C. Fully opened, upper surface: 143A to 143B. Fully opened, lower surface: 138A to 138B.

*Peduncles.*—Length: About 2.2 cm. Diameter: About 1 mm. Strength: Moderately strong. Angle: About 50° C. from vertical. Texture: Pubescent. Color: 144A; upper surface flushed with 177B to 177C.

*Pedicels.*—Length: About 2.9 cm. Diameter: About 1 mm. Strength: Moderately strong. Angle: About 15° C. from vertical. Texture: Pubescent. Color: N143A.

*Reproductive organs.*—Androecium: Stamen quantity per flower: About ten. Filament length: About 5 mm. Filament color: N86C. Anther length: About 2 mm. Anther width: About 1 mm. Anther shape: Oblong. Anther color: Between N186A and 202A. Pollen amount: Scarce. Pollen color: 12B. Gynoecium: Pistil quantity per flower: One. Pistil length: About 6 mm. Stigma shape: Five-parted; reflexed. Stigma color: N79B. Style length: About 4.5 mm. Style color: 144B. Ovary color: 144B to 144C.

*Seed.*—Seed development has not been observed.

Disease/pest resistance: Plants of the new *Geranium* have not been observed to be resistant to pathogens and pests common to *Geraniums.*

Garden performance: Plants of the new *Geranium* have exhibited good garden performance and to tolerate rain and wind and have been observed to be suitable for USDA Zone 5.

It is claimed:

1. A new and distinct *Geranium* plant named 'Thumbling Hearts' as illustrated and described.

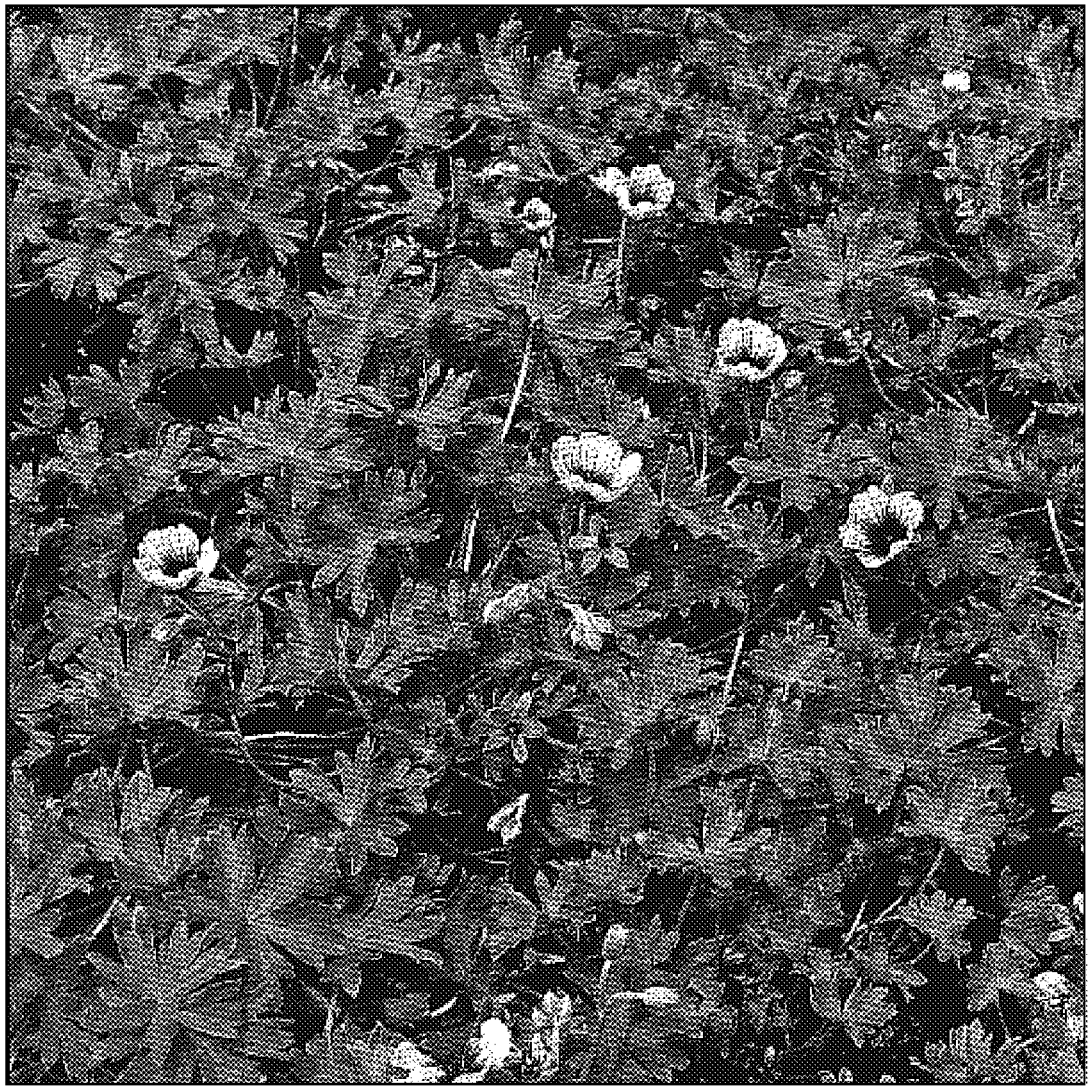

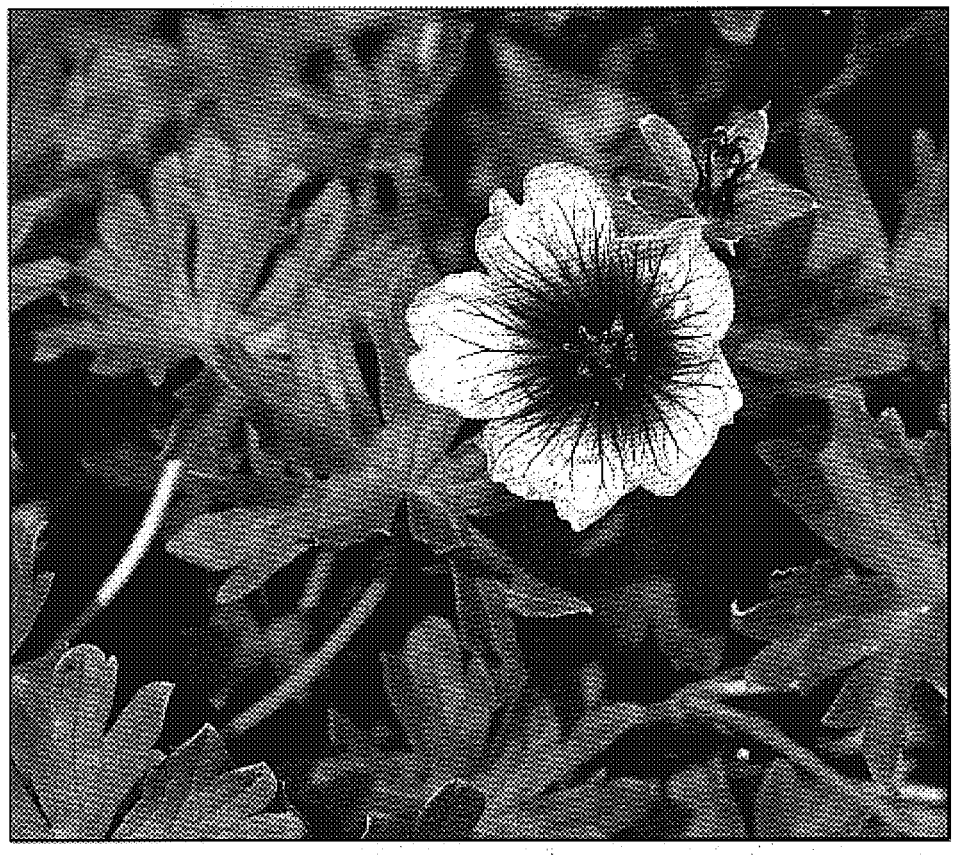
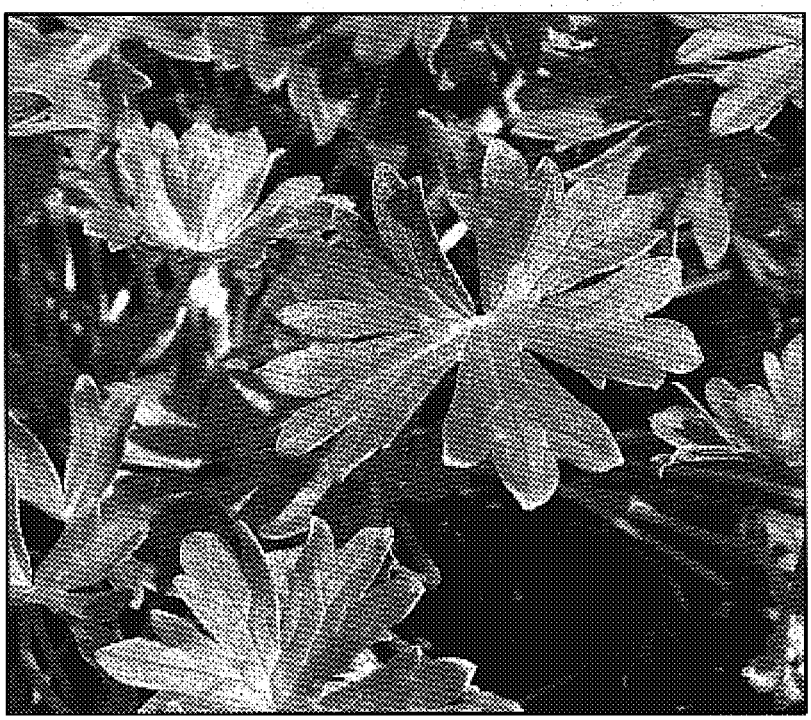

* * * * *